United States Patent [19]

De Vries et al.

[11] 4,228,015
[45] Oct. 14, 1980

[54] PLASMA TREATMENT APPARATUS

[75] Inventors: James H. De Vries, McHenry; Gaylord L. Berry, Mundelien, both of Ill.

[73] Assignee: Baxter Travenol Laboratories, Inc., Deerfield, Ill.

[21] Appl. No.: 7,487

[22] Filed: Jan. 29, 1979

[51] Int. Cl.² ............................................. B01D 13/00
[52] U.S. Cl. ................................ 210/321 R; 210/259; 210/434
[58] Field of Search ............ 210/321 A, 321 B, 321 R, 210/23 F, 22, 434, DIG. 23, 433 M, 259, 73

[56] References Cited

U.S. PATENT DOCUMENTS

| | | | |
|---|---|---|---|
| 3,491,021 | 1/1970 | Huntington | 210/23 F |
| 3,579,441 | 5/1971 | Brown | 210/434 |
| 3,591,493 | 7/1971 | Zeinch | 210/22 |
| 3,705,100 | 12/1972 | Blatt et al. | 210/23 F |
| 3,727,612 | 4/1973 | Sayers et al. | 210/321 B |
| 3,734,851 | 5/1973 | Matsumura | 210/22 |
| 3,827,565 | 8/1974 | Matsumura | 210/22 |
| 4,013,564 | 3/1977 | Nose | 210/434 |

OTHER PUBLICATIONS

Castino, et al. "Microemboli-Free Blood Detoxification Utilizing Plasma Filtration" XXII, Tran. Amer. Soc. Artif. In. Org., pp. 367-645, 1976.

*Primary Examiner*—Charles N. Hart
*Assistant Examiner*—E. Rollins Cross
*Attorney, Agent, or Firm*—H. W. Collins; Paul C. Flattery; George H. Gerstman

[57] ABSTRACT

A plasmapheresis system in which whole blood is filtered through a microporous membrane to provide a plasma filtrate. The system includes a filter cell assembly having a membrane support member, a treatment membrane spaced from the membrane support member with a plasma treatment agent sandwiched between the treatment membrane and the membrane support member, and a microporous membrane spaced from the treatment membrane to form a plasma chamber between the treatment membrane and the microporous membrane. Whole blood is introduced to the side of the microporous membrane opposite to the plasma chamber, plasma is filtered through the microporous membrane to the plasma chamber and the plasma filtrate contacts the treatment membrane which operates to provide a mass transfer between the treatment agent and the plasma filtrate. The treated plasma is withdrawn from the plasma chamber, is mixed with the plasma-poor whole blood and is returned to the patient.

13 Claims, 3 Drawing Figures

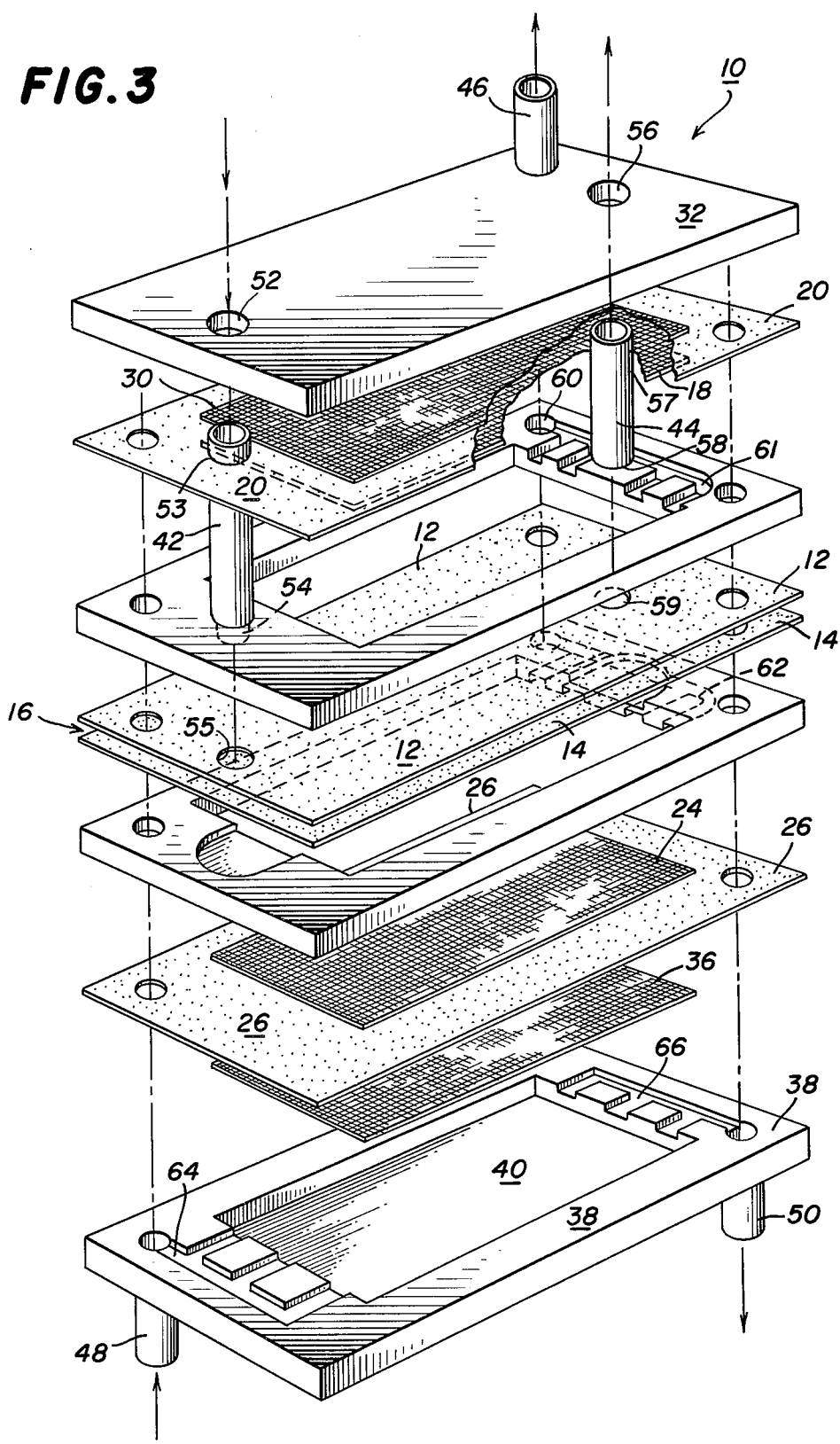

PLASMA TREATMENT APPARATUS

BACKGROUND OF THE INVENTION

This invention concerns a membrane plasmapheresis system in which the plasma filtrate is treated with an agent for detoxification, cleansing, transformation, reaction, elimination of matter, addition of matter, or any other treatment characteristic.

The use of microporous membranes for the separation of plasma has been found to be, on occasion, an extremely effective substitute for the centrifugal cell separator. The separation of plasma from whole blood through a microporous membrane, or membrane plasmapheresis as it is now commonly known, may be significantly less costly than centrifugal cell separation and may also have considerably greater efficiency.

A membrane plasmapheresis system in which a reactor compartment is formed between a pair of microporous membranes and plasma is filtered from whole blood through the first of the microporous membranes to enter the reactor compartment and then pass through the other microporous membrane is described in Castino, et al. "Microemboli—Free Blood Detoxification Utilizing Plasma Filtration", XXII, Trans. Amer. Soc. Artif. Int. Organs, pp. 367-645 (1976).

It has been discovered that it is often undesirable for the plasma to have direct contact with the treatment agent, such as by directly passing through the treatment agent as described in the Castino, et al. article. However, it is extremely desirable to utilize a system that permits simultaneous plasmapheresis and plasma treatment, in an efficient manner and utilizing a device that may be disposed of after use.

It is, therefore, an object of the present invention to provide a membrane plasmapheresis system that is simple in construction and relatively easy to manufacture.

Another object of the present invention is to provide a plasmapheresis apparatus that permits the treatment of the plasma without requiring the plasma to be filtered directly through a treatment reaction chamber.

A further object of the present invention is to provide a membrane plasmapheresis and plasma treatment apparatus that is capable of being formed as a disposable unit.

A still further object of the present invention is to provide a disposable plasmapheresis and plasma treatment cell that is structured to permit the dynamic flow of the plasma treatment agent during operation of the device.

Other objects and advantages of the present invention will become apparent as the description proceeds.

SUMMARY OF THE INVENTION

In accordance with the present invention, a plasma treatment apparatus is provided of the type in which whole blood is filtered through a microporous membrane having a pore size between 0.1 micron and 2 microns thereby providing a plasma filtrate. The improvement comprises a filter cell assembly including the microporous membrane with the filter cell assembly having a membrane support member and a treatment membrane supported by the membrane support member. A plasma treatment agent is sandwiched between the membrane support member and the treatment membrane. The treatment membrane is spaced from the microporous membrane to form a plasma chamber therebetween. The treatment membrane is operable to permit transfer between the treatment agent and the plasma in the plasma chamber. Means are provided for introducing whole blood to one side of the microporous membrane and means are provided for withdrawing treated plasma from the plasma chamber.

In the illustrative embodiment, the plasma treatment agent is circulated between the membrane support member and the treatment membrane.

In the illustrative embodiment, the plasma filter cell assembly is provided having a blood inlet, a blood outlet and a plasma outlet. A pair of microporous membranes form a blood flow path therebetween. A first membrane support member is positioned on one side of the pair of microporous membranes and a second membrane support member is positioned on the opposite side of the microporous membranes. A treatment membrane is positioned intermediate each of the membrane support members and one of the microporous membranes.

A plasma treatment agent is sandwiched between each membrane support member and treatment membrane. The blood inlet and blood outlet are coupled to the blood flow path between the microporous membranes and the plasma outlet is coupled to the plasma chambers.

A more detailed explanation of the invention is provided in the following description and claims, and is illustrated in the accompanying drawings.

BRIEF DESCRIPTION OF THE DRAWINGS

FIG. 3 is an exploded prospective view, with portions broken away for clarity, of a plasma treatment apparatus constructed in accordance with the principles of the present invention.

DETAILED DESCRIPTION OF THE ILLUSTRATIVE EMBODIMENT

Figure 1:
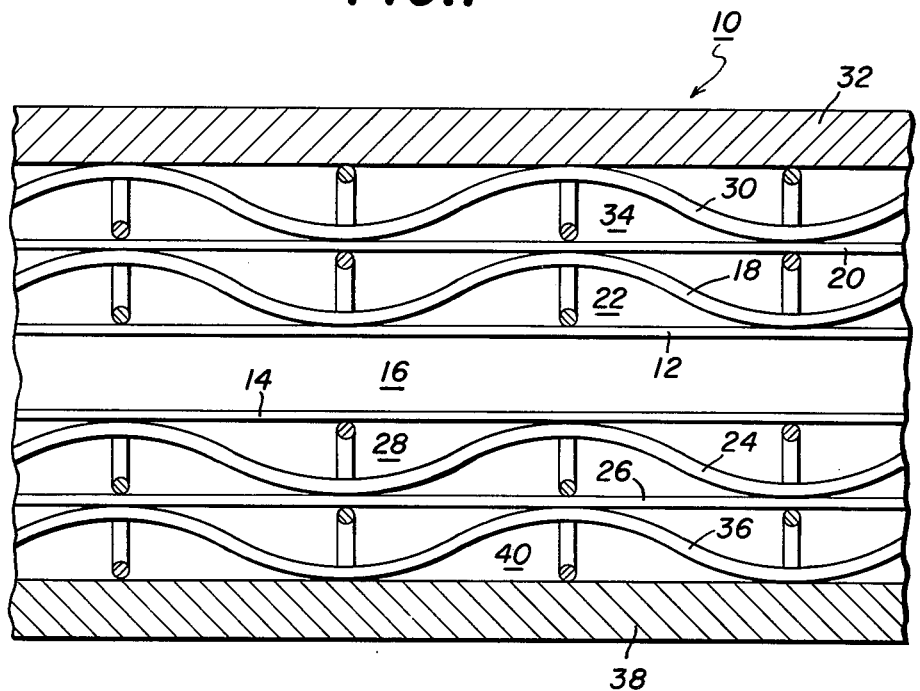
FIG. 1 is a fragmentary enlarged cross-sectional view of filter cell assembly constructed in accordance with the principles of the present invention.

Referring to the figures, a filter cell assembly 10 is illustrated. Filter cell 10 is preferably manufactured for disposability after use, utilizing extruded or molded plastic materials, with the filter cell assembly being attachable during use to a rigid, permanent holder. A type of permanent apparatus which could be used to hold filter cell assembly 10 is illustrated in FIG. 16 of co-pending application Ser. No. 942,077, filed Sept. 13, 1978 for "Apparatus For Membrane Plasmapheresis".

Filter cell assembly 10 includes a pair of spaced microporous membranes 12, 14 which form a blood flow path 16 therebetween. Membranes 12, 14 are the plasmapheresis membranes which filter through the plasma of the whole blood but which retain the cellular material. The membranes each have pore sizes between 0.1 micron and 2 microns, with the average pore size preferably being about 0.65 microns. Membranes 12, 14 have a void volume of greater than 60%, with an average void volume of about 80%. The membranes 12, 14 are preferably formed of a polymeric material, with the pores defining a relatively tortuous path. The thickness of each of the membranes 12, 14 is between 0.002 inch and 0.008 inch.

A mesh screen 18 separates membrane 12 from a mass transfer membrane 20, with a plasma chamber 22 being formed in the volume between membrane 12 and membrane 20. Likewise, a mesh screen 24 separates membrane 14 from a mass transfer membrane 26, with a plasma chamber 28 formed in the volume between membrane 14 and membrane 26.

Membranes 20 and 26 are preferably similar to the membranes used in dialysis and may be formed of conventional semi-permeable membrane, such as Cuprophan ®.

A mesh screen 30 separates membrane 20 from a membrane support member 32 with a treatment agent chamber 34 being formed in the volume defined by membrane 20 and membrane support member 32. Likewise, a mesh screen 36 separates membrane 26 from membrane support member 38, with treatment agent chamber 40 being formed in the volume defined by membrane 26 and membrane support member 38.

Figure 2:
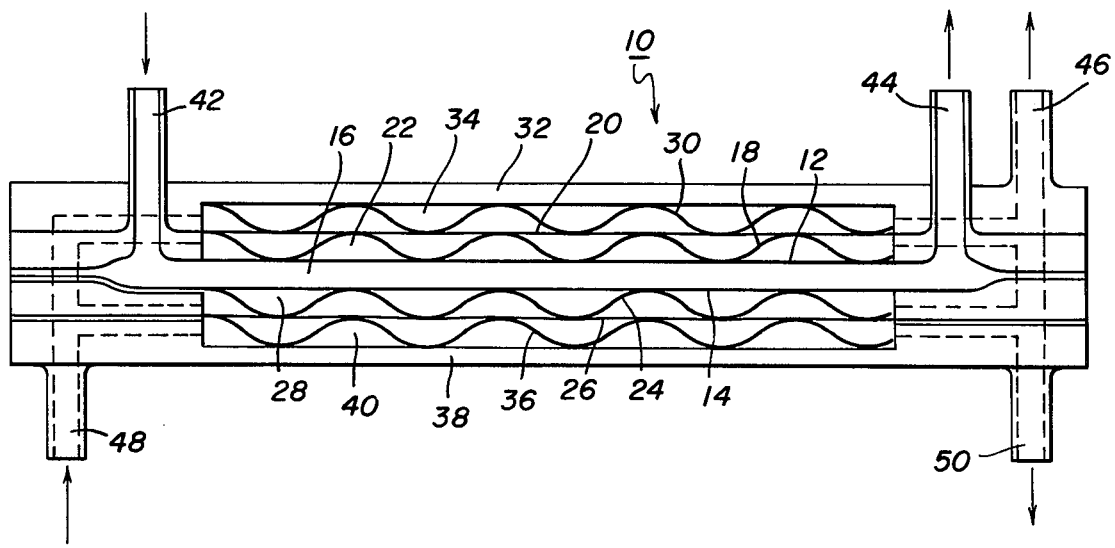
FIG. 2 is a diagrammatic view of a plasma treatment apparatus constructed in accordance with the principles of the present invention.

As shown most clearly in FIG. 2, a whole blood inlet 42 is provided in communication with blood flow path 16 and a blood outlet 44 is also provided in communication with blood flow path 16. A plasma outlet 46 is provided in communication with plasma filtrate chambers 22 and 28 for removing the plasma which has been treated. If desired, plasma outlet 46 may be coupled to blood outlet 44 so that the treated plasma is reunited with the plasma-poor blood in blood outlet 44 for reinfusion to a patient.

A plasma treatment agent is located in treatment agent chambers 34 and 40. Possible treating agents may include activated charcoal, ion exchange resins, immobilized antigen, or any other treating agent which is desired for use in treating the plasma.

Although the treating agent may be immobilized within chambers 34 and 40, it is preferred that the treating agent be circulated through these chambers in order for mass transfer between the agent and the plasma to be most efficient. To this end, a treating agent inlet 48 is located in communication with chambers 34 and 40 and a treating agent outlet 50 is also located in communication with chambers 34 and 40.

The communication between the inlet and outlet ports and the respective chambers is depicted in detail in FIG. 3. Referring to FIG. 3, blood inlet port 42 comprises a tube the outer circumference of which is sealed to apertures 52, 53, 54 and 55 so that the outlet of tube 42 extends into blood flow path 16 which is defined by membranes 12 and 14. Likewise, blood outlet port 44 comprises a tube which has its circumference sealed to the walls of apertures 56, 57, 58 and 59, with the inlet of port 44 lying within blood flow path 16.

Plasma collection port 46 is coupled to recess 60 to effectively collect the plasma collected within path 61 and also to collect the plasma within similar path 62, with path 61 and 62 being in communication with plasma collection chambers 22 and 28, respectively.

Treatment agent inlet 48 is coupled to path 64 while treatment agent outlet 50 is coupled to path 66. Paths 64 and 66 communicate with treatment agent chamber 40. Membrane support member 32 is identical to membrane support member 38 and thus the underside of membrane support member 32 (not shown) defines paths similar to paths 64 and 66 and also defines treatment agent chamber 34 which is similar in structure to treatment agent chamber 40. The apertures shown alined with treatment agent inlet 48 allow the treatment agent to flow into both treatment agent chambers 34 and 40 via the alined apertures, and the apertures which aline with treatment agent outlet 50, which are diagonally opposed to the apertures alined with treatment agent inlet 48, enable the treatment agent to flow through the chambers 34 and 40 and out of treatment agent outlet 50.

It can be seen that plasma treatment apparatus has been provided which provides for simultaneous plasmapheresis and treatment of the plasma filtrate, with the provision of a disposable filter cell suitable for use in continuous plasmapheresis such as disclosed in co-pending patent application Ser. No. 942,077, filed Sept. 13, 1978 and entitled "Apparatus for Membrane Plasmapheresis". By utilizing treatment agent chambers as described above, appropriate treatment agent may be pumped into the system and may be recycled and replenished as desired, with the opportunity to control the amount of treating agent that is being used as well as being able to control the transmembrane pressure. Utilizing such controls, the operator may obtain the desired mass transfer with respect to the plasma and the treating agent.

Although an illustrative embodiment of the invention has been shown and described, it is to be understood that various modifications and substitutions may be made by those skilled in the art without departing from the novel spirit and scope of the present invention.

What is claimed is:

1. Plasma treatment apparatus in which whole blood is filtered through a microporous membrane having a pore size between 0.1 micron and 2 microns thereby providing a plasma filtrate, the improvement comprising, in combination:
   a filter cell assembly including said microporous membrane;
   said filter cell assembly having a membrane support member and a treatment membrane supported by said membrane support member;
   a plasma treatment agent sandwiched between said membrane support member and said treatment membrane;
   said treatment membrane being spaced from said microporous membrane to form a plasma chamber therebetween;
   said treatment membrane being operable to permit transfer between said treatment agent and the plasma in said plasma chamber;
   means for introducing whole blood to one side of said microporous membrane; and
   means for withdrawing treated plasma from said plasma chamber.

2. Plasma treatment apparatus as described in claim 1, including means for circulating said plasma treatment agent between said membrane support member and said treatment membrane.

3. Plasma treatment apparatus as described in claim 1, including spacer means positioned between said treatment membrane and said microporous membrane.

4. Plasma treatment apparatus as described in claim 3, said spacer means comprising a mesh screen.

5. Plasma treatment apparatus as described in claim 1, said means for introducing whole blood including a blood inlet port and a blood outlet port communicating with said one side of said microporous membrane.

6. Plasma treatment apparatus as described in claim 2, said plasma treatment agent circulation means including a treatment agent inlet port and a treatment agent outlet port communicating with the volume defined by the treatment membrane and the membrane support member.

7. Plasma treatment apparatus in which whole blood is filtered through a microporous membrane having a pore size between 0.1 micron and 2 microns thereby providing a plasma filtrate, the improvement comprising, in combination:
- a filter cell assembly including said microporous membrane;
- said filter cell assembly having a membrane support membrane and a treatment membrane supported by said membrane support member;
- a plasma treatment agent sandwiched between said membrane support member and said treatment membrane;
- a treatment agent inlet port and a treatment agent outlet port communicating with the volume defined by the treatment membrane and the membrane support member for circulating said plasma treatment agent between said membrane support member and said treatment membrane;
- means positioned between said treatment membrane and said microporous membrane for spacing said microporous membrane from said treatment membrane to form a plasma chamber therebetween;
- said treatment membrane being operable to permit transfer between said treatment agent and the plasma in said plasma chamber;
- a blood inlet port and a blood outlet port communicating with one side of said microporous membrane for circulating blood to said one side of said microporous membrane; and
- means for withdrawing treated plasma from said plasma chamber.

8. Plasma treatment apparatus as described in claim 7, wherein said treatment membrane is spaced from said microporous membrane by a mesh screen.

9. Plasma treatment apparatus comprising:
- a filter cell assembly having a blood inlet, a blood outlet and a plasma outlet;
- a pair of microporous membranes forming a blood flow path therebetween;
- said microporous membranes having a pore size between 0.1 micron and 2 microns;
- a first membrane support member positioned on one side of said pair of microporous membranes and a second membrane support member positioned on the opposite side of said microporous membranes;
- a treatment membrane positioned intermediate each of said membrane support members and one of the microporous membranes;
- means for spacing each of said treatment membranes from the respective microporous membrane to form a plasma chamber between each of said treatment membranes and the respective microporous membrane;
- a plasma treatment agent sandwiched between each membrane support member and treatment membrane;
- means coupling said blood inlet and blood outlet to said blood flow path between said microporous membranes; and
- means coupling said plasma outlet to said plasma chambers.

10. Plasma treatment apparatus as described in claim 9, including a plasma treatment agent inlet and a plasma treatment agent outlet; means coupling said plasma treatment agent inlet and outlet to locations between each membrane support member and treatment membrane to form a circulation path for said plasma treatment agent.

11. Plasma treatment apparatus as described in claim 9, said spacing means comprising a mesh screen.

12. Plasma treatment apparatus as described in claim 9, said treatment membrane having a pore size that is less than 0.1 micron.

13. Plasma treatment apparatus comprising:
- a filter cell assembly having a blood inlet, a blood outlet and a plasma outlet;
- a pair of microporous membranes forming a blood flow path therebetween;
- said microporous membranes having a pore size between 0.1 micron and 2 microns;
- a first membrane support member positioned on one side of said pair of microporous membranes and a second membrane support member positioned on the opposite side of said microporous membranes;
- a treatment membrane positioned intermediate each of said membrane support members and one of the microporous membranes;
- means for spacing each of said treatment membranes from the respective microporous membrane to form a plasma chamber between each of said treatment membranes and the respective microporous membrane, said spacing means comprising a mesh screen;
- a plasma treatment agent sandwiched between each membrane support member and treatment membrane;
- a plasma treatment agent inlet and a plasma treatment agent outlet;
- means coupling said plasma treatment agent inlet and outlet to locations between each membrane support member and treatment membrane to form a circulation path for said plasma treatment agent;
- said treatment membrane having a pore size that is less than 0.1 micron;
- means coupling said blood inlet and blood outlet to said blood flow path between said microporous membranes; and
- means coupling said plasma outlet to said plasma chambers.

* * * * *